| United States Patent [19] | [11] Patent Number: 4,873,361 |
|---|---|
| Fjare | [45] Date of Patent: Oct. 10, 1989 |

[54] PROCESS FOR PRODUCTION OF P-ACETOXYBENZOIC ACID FROM P-ACETOXYACETOPHENONE

[75] Inventor: Krisati A. Fjare, Naperville, Ill.

[73] Assignee: Amoco Corporation, Chicago, Ill.

[21] Appl. No.: 237,992

[22] Filed: Aug. 29, 1988

Related U.S. Application Data

[63] Continuation-in-part of Ser. No. 16,746, Feb. 19, 1987, abandoned.

[51] Int. Cl.$^4$ ............................................. C07C 67/08
[52] U.S. Cl. .................................................. 560/130
[58] Field of Search ......................... 560/130; 562/421

[56] References Cited

U.S. PATENT DOCUMENTS 4,314,073  2/1982  Crooks .............................. 562/416
4,665,215  5/1987  Davenport ......................... 562/421

*Primary Examiner*—Michael L. Shippen
*Attorney, Agent, or Firm*—Gunar J. Blumberg; William H. Magidson; Ralph C. Medhurst

[57] ABSTRACT

A liquid-phase process is disclosed for oxidation of p-acetoxyacetophenone to p-acetoxybenzoic acid in high yield in a solvent in the presence of a catalyst and addition of a promoter comprising an acid anhydride of a lower aliphatic carboxytlic acid at an addition rate within specified mole ratio limits, a temperature within the range of from about 200° F. to about 400° F., and a pressure within the range of from about 1 atmosphere to 30 atmospheres. A first portion of the promoter is added at the start of the process, and a second portion of the promoter is added during the process.

17 Claims, No Drawings

PROCESS FOR PRODUCTION OF P-ACETOXYBENZOIC ACID FROM P-ACETOXYACETOPHENONE

CROSS-REFERENCE TO RELATED APPLICATION

This application is a continuation-in-part application of application Ser. No. 16,746, filed Feb. 19, 1987.

BACKGROUND OF THE INVENTION

The field of this invention relates to the liquid-phase oxidation of p-acetoxyacetophenone to p-acetoxybenzoic acid in high yield by the addition of acetic anhydride during the reaction, thus increasing the yield of reaction product by about 35% to about 40%. This invention also relates to the addition of acetic anhydride to the reaction as a reaction promoter to increase the yield of p-acetoxybenzoic acid, thus obtaining a more economical and efficient process. This invention also relates to the production of p-acetoxybenzoic acid by continuous, semicontinuous, or a batch process. The batch process is one where p-acetoxyacetophenone is introduced into the process at the beginning of the process and product is removed at the end of the process. The semicontinuous process is one where p-acetoxyacetophenone is added at one or more times during the course of the process, as well as at the beginning of the process, and product is removed at the termination of the process. The continuous process is one where p-acetoxyacetophenone is introduced into the process at the beginning of the process, as well as during the course of the process, and product is removed throughout the process.

The possibility of using liquid-phase instead of vapor-phase oxidation for the preparation of benzene carboxylic acids was first indicated by the disclosure in U.S. Pat. No. 2,245,528 of the catalysis provided by transition of variable valence metals, especially cobalt, in a liquid phase of saturated lower aliphatic acid at temperatures from 100° C. to 320° C. and pressures to maintain the liquid phase of the aliphatic acid. Such catalysis, according to said patent, was advantageously promoted by the use of a ketone, such as methylethyl ketone, or an aldehyde, such as acetaldehyde. Unfortunately, such aldehyde or ketone promoted variable valence metal catalysis was useful only for converting mono-, di- or trimethylbenzenes to their respective benzene monocarboxylic acids: benzoic, toluic and dimethyl benzoic acids. Two separate, later, and somewhat parallel lower temperature (80° C.–100° C.) modifications of the aldehyde or ketone promoted cobalt catalysis in liquid phase of acetic acid did provide commercially feasible conversion of xylenes to phthalic acids, especially p-xylene to terephthalic acid, but only at the expense of using rather high concentrations of cobalt with respect to p-xylene.

The disadvantages of using high concentrations of cobalt promoted with large quantities of aldehyde or ketone were overcome and, at the same time, a greater choice of variable valence metal oxidation catalysts was made available and a wider choice of alkyl-substituted benzene starting materials for benzene di-, tri- and higher carboxylic acids was provided by the discovery of the unique promotional effect on said variable valence metal by bromine ion, provided per se or formed in situ with or without acidic reaction medium provided by $C_1$–$C_8$ monocarboxylic acids having no hydrogens on a tertiary carbon, such as benzoic acid and the saturated aliphatic monocarboxylic acids, preferably acetic acid. Such bromine-variable valent metal catalysis was first disclosed in U.S. Pat. No. 2,833,816.

The bromine-polyvalent metal catalysis in acetic acid solvent has been in commercial use in many countries for the manufacture of benzene carboxylic acids and derivatives of benzene carboxylic acids for many years, such as terephthalic acid from p-xylene. However, for example, in the absence of acetic acid solvent, best yield of a single phthalic acid (e.g., terephthalic acid) on a once-through basis of the xylene, amounted to about 20 weight percent (12.8 mole), according to U.S. Pat. No. 2,833,816. According to U.S. Pat. No. 3,920,735 the Mn-Br and Co-Mn-Br catalyst system is improved by the addition of zirconium. However, not mentioned, but illustrated in Tables I, II and IV in U.S. Pat. No. 3,920,735, is the fact that, when part of the zirconium is added, combustion of the feedstock to carbon dioxide increases.

The preparation of acyloxy aromatic carboxylic acids by oxidation of acyloxy aromatic ketones with oxygen in the presence of a catalyst and coreductant has been taught. According to EP Patent Application No. 170483, preparation of acyloxy aromatic carboxylic acids is accomplished by oxidation with oxygen of acyloxy aromatic ketones R—C(O)O—Ar—C(O)R employing a transition metal catalyst and coreductant where Ar is a divalent aromatic radical, preferably 1,4-phenylene, R is preferably the same or it may be different and contain from 1 to 18 carbon atoms. The acyloxy aromatic ketone, 4-acetoxyacetophenone and its oxidized product, 4-acetoxybenzoic acid, is prepared. The claimed catalyst and coreductant are manganese ions and acetaldehyde, respectively.

The preparation of p-acetoxybenzoic acid from p-cresyl acetate with oxygen in the presence of bromine and a catalytic mixture comprising a cobalt compound and a manganese compound has been disclosed. However, yields are low and the aldehyde is produced in quantity. According to Japanese Patent No. SHO 50-35066, in Table II, in the oxidation of p-cresyl acetate with oxygen in the presence of a bromine compound, cobalt acetate and manganese acetate wherein acetic acid and acetic anhydride were employed as solvents, yield of acetoxybenzoic acid was 42.3 mole % and yield of acetoxybenzaldehyde was 12.4 mole %. In the absence of acetic anhydride, yield of acetoxybenzoic acid was 39.6 mole % and yield of acetoxybenzaldehyde was 21.2 mole %. In the absence of acetic acid, yields dropped to 12.6 mole % and 7.2 mole %. Unreacted feed material, moreover, was sizeable, ranging from 37.5 mole % in the absence of acetic anhydride, to 55.8 mole % in the absence of acetic acid, and being 42.1 mole % when both solvents, acetic acid and acetic anhydride were present.

Despite earlier evidence, as disclosed in U.S. Pat. No. 2,245,528 and EP Patent Application No. 170483, that the presence of a ketone was useful as a promoter in the oxidation of mono-, di-, or trimethyl benzenes to their respective monocarboxylic acids, or a coreductant was useful in the oxidation of acetoxyacetophenone to acetoxybenzoic acid in the oxidation of the respective feed materials with oxygen in the presence of transition metals, especially cobalt, it has been found unexpectedly that liquid-phase oxidation of an acetoxylated benzylic ketone to an acetoxybenzene monocarboxylic acid can be obtained in advantageous yields in a solvent of a lower aliphatic saturated carboxylic acid in the presence of a catalyst mixture comprising a mixture of transition metals, a bromine compound, and alternatively, a zirconium compound, and a promoter consisting essentially of an anhydride of the same carboxylic acid used as solvent.

SUMMARY OF THE INVENTION

A novel process for preparation of p-acetoxybenzoic acid from p-acetoxyacetophenone has been discovered. The process comprises liquid-phase oxidation of p-acetoxyacetophenone in the presence of a catalytic mixture comprising a bromine compound, a cobalt compound, and a manganese compound, a promoter comprising the anhydride of a saturated carboxylic acid, in a solvent comprising the said saturated carboxylic acid. The catalyst can also comprise a zirconium compound. This new process provides a high product yield of 85 mole % to 88 mole % of p-acetoxybenzoic acid. Unreacted feed material is in the range of from about 3 mole % to about 5 mole %. Production of by-products is minimized. Recycle of mother liquor from a product recovery system can increase product yield. The process can be operated in a batch method, a semicontinuous method, or in a continuous method.

DETAILS OF THE INVENTION

The invented process for preparation of p-acetoxybenzoic acid (pABA) from p-acetoxyacetophenone (pAAP) can be by batch, semicontinuous, or continuous method. In a commercial operation, a semicontinuous method is preferred.

In the batchwise oxidation of p-acetoxyacetophenone, the exothermic heat of reaction vaporizes some of the liquid solvent which is carried out of the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and p-acetoxybenzoic acid is crystallized out to form a 15%–20% solids slurry. The slurry is concentrated by evaporation and further processed into final product by filtration and recrystallization. The filtrate is recycled.

In this novel process, acetic acid with acetic anhydride promoter is added to the reactor in precise ratios to maintain the required mole ratio of promoter (acetic anhydride) to p-acetoxyacetophenone (pAAP). It is essential for high yield that acetic anhydride be added to the reactor during the process to maintain the required ratio of anhydride to p-acetoxyacetophenone.

The metal oxidation catalyst components are cobalt, zirconium, and manganese, or cobalt and manganese. Total metal concentration based on pAAP is preferably in the range of about $1.0 \times 10^{-8}$ to about $4.0 \times 10^{-2}$ moles per mole of p-acetoxyacetophenone, most preferably $3.0 \times 10^{-2}$ moles per mole of p-acetoxyacetophenone. Below a catalyst concentration of $1.0 \times 10^{-8}$, yield of product is reduced significantly, although product can be prepared. A catalyst concentration above $4.0 \times 10^{-2}$ is uneconomic and wastes catalyst. The metal concentration is in combination with a source of bromine providing a bromine to total metal ratio of about 1.3 to about 5.0, preferably about 1.4 to about 4.5, on a weight basis. The manganese component of the catalyst is in the range of about 45 to about 55 weight percent based on the total weight of catalyst metals. The zirconium content of the total metals used is in the range of about 1.0% to about 5.0%, preferably about 1.5% to about 2.5% by weight of total metals. The cobalt component of the catalyst is in the range of about 45 to about 55 weight percent of the total metals.

The lower aliphatic saturated carboxylic acid useful as a solvent can be selected from either acetic acid or propionic acid and the promoter can be either acetic anhydride or propionic anhydride. Acetic acid and promoter of acetic anhydride is preferred.

In an alternative procedure, p-hydroxyacetophenone can be the starting material. p-Hydroxyacetophenone is esterified by reaction with an acid or acid anhydride, preferably a lower aliphatic carboxylic acid anhydride, more preferably acetic anhydride, to prepare p-acetoxyacetophenone. The reaction can be in the same reactor as is later used for oxidation of the p-acetoxyacetophenone.

The source of molecular oxygen can be air or any other source of oxygen which is economic and convenient. Air is preferred because of economics and ease of handling.

When the oxidation of pAAP is conducted batchwise, with acetic acid and acetic anhydride, the acid and anhydride are premixed in a separate reactor. Ratio of acid to anhydride is in the range of from about 4.0–5.0:1 moles, acid to anhydride, preferably 4.25:1 moles. The mixture of acid and anhydride is added to pAPP wherein ratio of anhydride to pAAP is about 1.05 moles anhydride to 1 mole pAAP. Catalyst comprising cobalt and manganese, and bromine, and, alternatively, zirconium is added with starting materials.

The total bromine added can be from a single source of bromine, for example, ionic bromine sources (HBr, NaBr, NH$_4$Br and the like) or from a combined form of bromine, for example, organic bromides such as benzyl bromide, tetrabromoethane and others.

In a specific embodiment, all components are charged to the reactor at a near oxidation initiation temperature, preferably at about 120° C. to about 200° C. and at a pressure to maintain liquid-phase conditions. Then, pressurized air is injected into the reaction mixture and the reaction temperature is permitted to increase by heat evolved by the oxidation reaction to about 175° C. to 225° C.

This novel process relates to the liquid-phase oxidation of pAAP to pABA using cobalt, manganese and/or other variable valence metals, such as zirconium plus bromine. A useful catalyst for the process is a zirconium-cobalt-manganese-bromine catalyst wherein the molecular ratio of zirconium to cobalt is about 1 to about 10 to about 1 to about 40 and the oxidation is conducted at a temperature in the range of about 200° F. to about 400° F.

In one preferred embodiment of the process for the oxidation of pAAP with molecular oxygen to pABA under liquid-phase conditions in the presence of a zirconium-cobalt-manganese-bromine catalyst, the molecular ratio of zirconium to cobalt is about 1:10 to about 1:40 and the temperature is in the range of about 200° F. to about 400° F.

This novel process also relates to the liquid-phase oxidation of pAAP wherein the catalyst mixture essentially comprises cobalt, manganese and bromine, to the exclusion of zirconium. The exclusion of zirconium reduces the activity of the catalyst mixture slightly by reducing combustion of the feedstock to carbon dioxide. Choice and decision as to use of zirconium-containing catalyst mixtures will be subject to the economics of the two alternative procedures.

In a semicontinuous or continuous process, reactor effluent is evaporated to remove water and acetic acid. Recovered acetic acid from reactor effluent is recycled to the make-up vessel of acetic anhydride and acetic acid. The bottoms from the evaporator, containing the reactor product, are filtered to remove acetic anhydride, acetic acid and catalyst in the mother liquor. The mother liquor is then recycled. The filter cake can be recrystallized to improve purity from a suitable solvent which can be water, acetic acid, or an aromatic hydrocarbon.

The instant invention accordingly comprises a liquid-phase process for production of p-acetoxybenzoic acid in high yield, which process comprises: a) oxidation of p-acetoxyacetophenone with a source of molecular oxygen in the presence of a catalyst comprising a cobalt(II) compound, a manganese(II) compound, and a bromine compound, in a solvent comprising a lower aliphatic carboxylic acid and in the presence of a promoter consisting essentially of an acid anhydride of said lower aliphatic carboxylic acid, at a temperature within the range of from about 200° F. to about 400° F. and at a pressure of from 1 atmosphere to about 30 atmospheres, and (b) said promoter is present as an initial reactor charge in a mole ratio to said p-acetoxyacetophenone of from 1.0:1 to about 2.4:1, and (c) said promoter is added to said reactor charge during said oxidation in an amount of from 0.25 to 1.5 moles per mole of said p-acetoxyacetophenone wherein total of said initial charge plus addition of said promoter is from about 1.6:1 to 3.0:1 moles of said promoter to said p-acetoxyacetophenone.

In view of this, there is provided an improved process for the production of p-acetoxybenzoic acid. In this improved liquid-phase process for the production of p-acetoxybenzoic acid from p-acetoxyacetophenone in high yield, wherein said p-acetoxyacetophenone is oxidized with a source of molecular oxygen in a reaction zone in the presence of a catalyst comprising cobalt, manganese, and bromine, in a solvent comprising a lower aliphatic carboxylic acid and in the presence of a promoter consisting essentially of an acid anhydride of said lower aliphatic carboxylic acid, said process being a semicontinuous or continuous process, the improvement comprises adding a first portion of said promoter as an initial reactor charge to said reaction zone and adding a second portion of said promoter to said reaction zone during the oxidation of said p-acetoxyacetophenone.

The catalyst can contain also, in addition to a cobalt-(II) compound, a manganese(II) compound, and a bromine compound, a zirconium compound.

The concentration of the said catalyst mixture can be in the range of from about $1.0 \times 10^{-8}$ moles to $4.0 \times 10^{-2}$ moles per mole of p-acetoxyacetophenone.

In one embodiment of the present invention, there is provided a semicontinuous or continuous liquid-phase process for the production of p-acetoxybenzoic acid from p-acetoxyacetophenone in high yield, which process comprises: (a) oxidizing in a reaction zone said p-acetoxyacetophenone with a source of molecular oxygen in the presence of a catalyst comprising cobalt-(II), manganese (II), and bromine, in a solvent comprising a lower aliphatic carboxylic acid and in the presence of a promoter consisting essentially of an acid anhydride of said lower aliphatic carboxylic acid, at a temperature within the range of from about 200° F. to about 400° F. and at a pressure of from 1 atmosphere to about 30 atmospheres, said promoter being present as an initial reactor charge in a mole ratio of promoter to said p-acetoxyacetophenone of from 1:1 to 2.4:1; (b) adding said promoter to said reaction zone during said oxidizing in an amount of from 0.2 to 1.5 moles of said promoter per mole of said p-acetoxyacetophenone, the total amount of promoter resulting from the initial charge and subsequent addition of said promoter providing a mole ratio of said promoter to said p-acetoxyacetophenone that is within the range of about 1.6:1 to 3:1 moles of said promoter per mole of said p-acetoxyacetophenone; (c) evaporating the reactor effluent to remove water and said lower aliphatic carboxylic acid therefrom; (d) recovering said lower aliphatic carboxylic acid that has been removed from said effluent; (e) recycling to a make-up vessel the lower aliphatic carboxylic acid that has been recovered from said effluent, (f) filtering the evaporator bottoms to recover reactor product from mother liquor; and (g) recycling said mother liquor to said reaction zone.

The original charge of said anhydride can be in the range of from about 1.0:1 to 1.8:1 moles of said anhydride per mole of p-acetoxyacetophenone. The said lower aliphatic saturated aliphatic acid is selected from the group consisting of acetic acid and propionic acid. The said anhydride is selected from the group consisting of acetic anhydride and propionic anhydride. Preferably, the said source of molecular oxygen comprises air. Preferably, the said process is a semicontinuous process. More preferably, the said process is a semicontinuous process, process temperature is in the range of from about 200° F. to about 350° F. and pressure is in the range of from about 1 atmosphere to about 20 atmospheres.

Alternatively, the said process can be a batch process, wherein process temperature is in the range of from about 200° F. to about 350° F. and pressure is in the range of from about 1 atmosphere to about 20 atmospheres, or the said process can be a continuous process, process temperature in the range of from about 200° F. to about 350° F. and pressures in the range of from about 1 atmosphere to about 20 atmospheres.

The novel process is exemplified by the following examples. These examples are exemplary only and are not meant to be construed as limiting.

EXAMPLE I

One hundred and sixty-six (166) g (0.933 mole) of p-acetoxyacetophenone, 100 g (0.98 mole) of acetic anhydride, 250 g (4.17 moles) of acetic acid, 3.5 g (0.014 mole) of $Co(C_2H_3O_2)_2.4H_2O$, identified hereinafter as $Co(OAc)_2.4H_2O$, 3.5 g (0.014 mole) of $Mn(C_2H_3O_2)_2.4H_2O$, identified hereinafter as $Mn(OAc)_2.4H_2O$ and 4.7 g (0.028 mole) 48% HBr were combined in a two-liter titanium-clad autoclave. The reaction mixture was heated to 300° F. and pressurized to 300 psi. Air was introduced at a rate of 0.75 scf/min. During the reaction, a mixture of 120 g (1.18 moles) of acetic anhydride and 30 g (0.5 mole) of acetic acid was added through a pump. The oxidation run time was 24 minutes. The reaction yields from analyses of the total reactor effluent and wash were: p-acetoxybenzoic acid, 86 mole %, p-hydroxybenzoic acid, 0.6 mole %, and unreacted p-acetoxyacetophenone, 4.5 mole %.

EXAMPLE II

The oxidation of p-acetoxyacetophenone proceeded as in Example I, except that the reaction was run for 30 minutes and a total of 150 g (1.47 moles) of acetic anhydride and 37 g (0.62 mole) of acetic acid was added through the pump. The reaction mixture was concentrated from 772 g to 413 g by evaporation of acetic acid. The slurry was filtered to remove precipitated p-acetoxybenzoic acid. After drying, 128.2 g of p-acetoxybenzoic acid of 95 mole % purity (73% yield) were obtained. Remaining in the filtrate were: p-acetoxybenzoic acid, 8.5 mole % yield, p-acetoxyacetophenone, 1.8 mole % yield, p-hydroxybenzoic acid, 0.6 mole % yield. Analysis of the reactor wash showed 2.6 mole % p-acetoxybenzoic acid. Total reaction yield of p-acetoxybenzoic acid was 84 mole %.

EXAMPLE III

One hundred and sixty-six (166) g (0.933 mole) of p-acetoxyacetophenone, 100 g (0.98 mole) of acetic anhydride, 250 g (4.17 moles) of acetic acid, 3.5 g (0.014 mole) Co(OAc)$_2$.4H$_2$O, 3.5 g (0.014 mole) of Mn(OAc)$_2$.4H$_2$O, and 4.7 g (0.028 mole) of 48% HBr were combined in a two-liter titanium-clad autoclave. The mixture was heated to 300° F. and pressurized to 300 psi. Air was introduced at a rate of 0.75 scf/min. During the run, a solution of 26 g (0.25 mole) of acetic anhydride and 6 g (0.1 mole) of acetic acid was added. The run time of the reaction was 24 minutes. Analyses of the total reactor effluent and wash gave: 78 mole % p-acetoxybenzoic acid, 8 mole % p-hydroxybenzoic acid, and 3.5 mole % unreacted p-acetoxyacetophenone.

EXAMPLE IV

One hundred and sixty-six (166) g (0.933 mole) of p-acetoxyacetophenone, 100 g (0.98 mole) of acetic anhydride, 250 g (4.17 moles) of acetic acid, 1.2 g (0.0048 mole) of Co(OAc)$_2$.4H$_2$O, 1.2 g (0.0049 mole) of Mn(OAc)$_2$.4H$_2$O, and 1.6 g (0.01 mole) of 48% HBr were combined in a two-liter titanium-clad autoclave. The mixture was heated to 300° F. and pressurized to 300 psi. Air was introduced at a rate of 0.75 scf/min for the first fifteen minutes and then lowered to 0.63 scf/min for the remainder of the reaction. During the oxidation, a mixture of 140 g (1.37 moles) of acetic anhydride and 35 g (0.58 mole) of acetic acid was added through a pump. The oxidation ran for 31 minutes. The reaction solution was cooled and evaporated from 678 g to 579 g. The precipitated p-acetoxybenzoic acid was filtered and dried to yield 106 g with a purity of 96.4 mole % (61 mole % yield). Analysis of the filtrate showed: p-acetoxybenzoic acid, 18.2 mole %, p-acetoxyacetophenone, 2.4 mole %, p-hydroxybenzoic acid, 1.3 mole %. Analysis of the reactor wash showed p-acetoxybenzoic acid, 2.2 mole %. Total reaction yield of p-acetoxybenzoic acid was 81.4 mole %.

EXAMPLE V

One hundred and sixty-six (166) g (0.933 mole) of p-acetoxyacetophenone, 100 g (0.98 mole) of acetic anhydride, 250 g (4.17 moles) of acetic acid, 0.35 g (0.0014 mole) of Co(OAc)$_2$.4H$_2$O, 0.35 g (0.0014 mole) of Mn(OAc)$_2$.4H$_2$O, and 0.47 g (0.0028 mole) of 48% HBr were combined in a two-liter titanium-clad autoclave. The mixture was heated to 300° F. and pressurized to 300 psi. Air was introduced at a rate of 0.75 scf/min for 15 minutes and then lowered to 0.61 scf/min for the remainder of the reaction. During the run, a solution of 150 g (1.47 moles) of acetic anhydride and 38 g (0.63 mole) of acetic acid was added through a pump. The run time was 31 minutes. The reaction solution was concentrated by evaporating acetic acid from 696 g to 660 g. The precipitated p-acetoxybenzoic acid was isolated by filtration and dried to give 81.3 g of 97.6 mole % purity (47.2 mole % yield). Analysis of the filtrate showed: p-acetoxybenzoic acid, 32 mole %, p-hydroxybenzoic acid, 0.3 mole %, and p-acetoxyacetophenone, 3.2 mole %. Analysis of the reactor wash showed p-acetoxyacetophenone, 2.1 mole %. Total reaction yield of p-acetoxybenzoic acid was 81.3 mole %.

EXAMPLE VI

One hundred and sixty-six (166) g (0.933 mole) of p-acetoxyacetophenone, 100 g (0.98 mole) of acetic anhydride, 250 g (4.17 moles) of acetic acid, 3.5 g (0.0014 mole) of Co(OAc)$_2$.4H$_2$O, 3.5 g (0.0014 mole) of Mn(OAc)$_2$.4H$_2$O, and 4.7 g (0.0028 mole) of 48% HBr were combined in a two-liter titanium-clad autoclave. The reaction mixture was heated to 300° F. and pressurized to 300 psi. Air was introduced at a rate of 0.75 scf/min. During the run, a solution of 54 g (0.53 mole) of acetic anhydride and 13 g (0.217 mole) of acetic acid was added through a pump. The run time was 25 minutes. Analyses of the total reactor effluent and wash showed: p-acetoxybenzoic acid, 87 mole % yield, p-hydroxybenzoic acid, 1.2 mole % yield, and p-acetoxyacetophenone, 3.5 mole % yield.

EXAMPLE VII

Seventeen and one-tenth (17.1) g (0.096 mole) of p-acetoxyacetophenone, 17.1 g (0.17 mole) of acetic anhydride, 65 g (1.08 moles) of acetic acid, 0.51 g (0.002 mole) of Co(OAc)$_2$.4H$_2$O, 0.50 g (0.002 mole) of Mn(OAc)$_2$.4H$_2$O, and 0.68 g (0.004 mole) of 48% HBr were combined in a glass reactor and heated to 100° C. Air was introduced at a rate of 50 ml/min. After 164 hours of reaction time, the oxidation ceased. Analysis of the reaction solution showed 3.4 wt % p-acetoxyacetophenone and 2.7 wt % p-hydroxyacetophenone. In addition, p-acetoxybenzoic acid and p-hydroxybenzoic acid were present in substantial amounts. An additional 30 g (0.294 mole) of acetic anhydride were added and the oxidation reaction continued. Final reaction time was 240 hours. Analysis of the final reaction mixture showed 41 mole % yield of p-acetoxybenzoic acid, 3.9 mole % yield of p-hydroxybenzoic acid, and 1.0 mole % yield unreacted p-acetoxyacetophenone.

EXAMPLE VIII

In the batch procedure of Example I, five reactions were run with different ratios of acetic anhydride to p-acetoxyacetophenone, wherein acetic anhydride was added during the reaction. The decrease in the addition of benzoic acid and increased the yield of by-product p-hydroxybenzoic acid (pHBA). Reduced presence of total moles of Ac$_2$O to pAAP of 1.32 increased undesired by-product, p-hydroxybenzoic acid, to a level of 8 mole %. Results are in Table I.

TABLE I

Addition of Acetic Anhydride (Ac₂O) To Oxidation of pAAP

| Run No. | Ac₂O Added Moles Ac₂O/ pAAP | Total Moles Ac₂O/ pAAP | Yield pABA Mole % | Yield pHBA Mole % | Unreacted pAAP Mole % |
|---|---|---|---|---|---|
| 105 | 1.26 | 2.31 | 86 | .6 | 4.5 |
| 107 | 1.43 | 2.48 | 87 | <1.0 | 3.5 |
| 115 | 1.35 | 2.40 | 85 | .6 | 4.0 |
| 109 | 0.27 | 1.32 | 78 | 8.0 | 3.5 |
| 111 | 0.57 | 1.62 | 87 | 1.2 | 3.5 |

Note:
Initial reactor charge: Mole ratio of acetic anhydride: pAAP was 1.05:1. Catalyst concentration (Co + Mn)/pAAP was $3.0 \times 10^{-2}$ moles/mole. pHBA is p-hydroxybenzoic acid.

EXAMPLE IX

In the procedure of Example I, seven process runs were made and compared on the basis of catalyst concentration. Catalyst concentration was determined as less significant than rate of addition of acetic anhydride as shown in Example VIII in Table I. Results are in Table II.

TABLE II

Catalyst Concentration-Oxidation of pAAP

| Run No. | Ac₂O Addition Ac₂O/ pAAP, Moles | Catalyst Concentration pAAP/ Moles ($\times 10^{-2}$) | Yield pABA Mole % | Yield pHBA Mole % | Unreacted pAAP Mole % |
|---|---|---|---|---|---|
| 105 | 1.26 | 3.0 | 86 | .6 | 4.5 |
| 107 | 1.43 | 3.0 | 87 | <1.0 | 3.5 |
| 115 | 1.35 | 3.0 | 85 | .6 | 4.0 |
| 125 | 1.58 | 3.0 | 84 | .7 | 1.8 |
| 127 | 1.41 | 1.0 | 81 | 1.3 | 3.2 |
| 129 | 1.47 | 1.0 | 81 | 1.3 | 2.4 |
| 131 | 1.58 | 0.3 | 81 | .3 | 3.2 |

EXAMPLE X

In the procedure of Example I, a p-acetoxyacetophenone was oxidized to p-acetoxybenzoic acid but in a semicontinuous method wherein p-acetoxyacetophenone (pAAP), acetic acid (HAc), and acetic anhydride (Ac₂O) were added to the reactor semicontinuously during the process. Process data and results are in Tables III an IV.

TABLE III

Semicontinuous Oxidation Of p-Acetoxyacetophenone To p-Acetoxybenzoic Acid

| Run No. | 184 | 186 | 196 | 198 | 4 |
|---|---|---|---|---|---|
| Reactor Charge, g | | | | | |
| p-Acetoxyacetophenone | 0 | 0 | 0 | 15 | 15 |
| Acetic Acid | 250 | 250 | 250 | 250 | 250 |
| Acetic Anhydride | 100 | 100 | 100 | 100 | 100 |
| Co(OAc)₂.4H₂O | 0.35 | 0.35 | 3.5 | 3.5 | 0.35 |
| Mn(OAc)₂.4H₂O | 0.35 | 0.35 | 3.5 | 3.5 | 0.35 |
| 48% HBr | 0.47 | 0.47 | 4.7 | 4.7 | 0.47 |
| Material Added Semicontinuously, g | | | | | |
| p-Acetoxyacetophenone | 184 | 183 | 183 | 167 | 153 |
| Acetic Acid | 39 | 39 | 39 | 39 | 46 |
| Acetic Anhydride | 161 | 160 | 160 | 160 | 184 |
| Time Required for Semicontinuous Addition, minutes | 47 | 34 | 45 | 55 | 38 |
| Reaction Temp., °F. | 350 | 350–395 | 350 | 300 | 350 |
| Run Time, minutes | 65 | 35 | 55 | 65 | 65 |
| CO₂, moles | 0.84 | NM[c] | 0.84 | 1.1 | 0.76 |
| CO, moles | NA[b] | NM | NA | NA | NA |
| Reactor Yield,[a] mole % | | | | | |
| p-Acetoxybenzoic Acid | 61 | 64 | 50 | 74 | 57 |
| p-Hydroxybenzoic Acid | 0.9 | 0.2 | 2.3 | 2.2 | 0.5 |
| p-Acetoxyacetophenone | 13 | 12 | 5.9 | 3.5 | 15 |
| p-Hydroxyacetophenone | 0.4 | ND[d] | 0.2 | 0.1 | 0.3 |
| Total, Mole % | 75 | 76 | 58 | 80 | 73 |

| Run No. | 6 | 8 | 10 | 12 | 14 |
|---|---|---|---|---|---|
| Reactor Charge, g | | | | | |
| p-Acetoxyacetophenone | 15 | 15 | 15 | 15 | 15 |
| Acetic Acid | 250 | 250 | 250 | 250 | 250 |
| Acetic Anhydride | 100 | 100 | 15 | 15 | 15 |
| Co(OAc)₂.4H₂O | 0.35 | 0.35 | 0.35 | 0.35 | .35 |
| Mn(OAc)₂.4H₂O | 0.35 | 0.35 | 0.35 | 0.35 | .35 |
| 48% HBr | 0.47 | 0.47 | 0.47 | 0.47 | .47 |
| Material Added Semicontinuously, g | | | | | |
| p-Acetoxyacetophenone | 153 | 157 | 165 | 165 | 167 |
| Acetic Acid | 46 | 47 | 38 | 38 | 25 |
| Acetic Anhydride | 184 | 188 | 251 | 251 | 166 |
| Time Required for Semicontinuous Addition, minutes | 38 | 40 | 20 | 20 | 20 |
| Reaction Temp., °F. | 30 | 300 | 300 | 350 | 300 |
| Run Time, minutes | 70 | 70 | 57 | 48 | 53 |
| CO₂, moles | 0.74 | 0.81 | 0.64 | 0.81 | 0.55 |
| CO, moles | NA | 1.01 | 0.88 | 1.06 | 0.81 |
| Reactor Yield,[a] mole % | | | | | |
| p-Acetoxybenzoic Acid | 81 | 82 | 81 | 76 | 81 |
| p-Hydroxybenzoic Acid | 0.4 | 0.3 | 0.4 | 0.6 | 0.8 |
| p-Acetoxyacetophenone | 3.4 | 2.7 | 2.9 | 4.2 | 4.9 |
| p-Hydroxyacetophenone | 0.1 | ND | ND | ND | 0.03 |
| Total, Mole % | 85 | 85 | 84 | 81 | 87 |

[a]Sum of filter cake, mother liquor, and wash analyses. Materials analyzed by gas chromatography (GC) and liquid chromatography (LC).
[b]Not analyzed.
[c]Not measured.
[d]Not detected.

TABLE IV

Effect of Addition of Ac₂O On pABA Yield

| Run No. | Mole Ratio Start | Addition Mole Ratio | Total Mole Ratio | Temp. °F. | Yield pABA Mole % |
|---|---|---|---|---|---|
| 4 | 11.6:1 | 2.1:1 | 2.95 | 350 | 57 |
| 6 | 11.6:1 | 2.1:1 | 2.95 | 300 | 81 |
| 8 | 11.6:1 | 2.1:1 | 2.95 | 300 | 82 |
| 10 | 1.7:1 | 2.66:1 | 2.57 | 300 | 81 |
| 12 | 1.7:1 | 2.66:1 | 2.57 | 350 | 76 |
| 14 | 1.7:1 | 1.7:1 | 1.74 | 300 | 81 |
| 184 | 0.98:0 | 1.52:1 | 2.57 | 350 | 62 |
| 186 | 0.98:0 | 1.52:1 | 2.57 | 350–395 | 64 |
| 196 | 0.98:0 | 1.52:1 | 2.57 | 350 | 50 |
| 198 | 11.6:1 | 1.67:1 | 2.57 | 300 | 74 |

Table IV illustrates that the method of addition and amount of addition of Ac₂O, coupled with the effect of reaction temperature unexpectedly increases the yield of p-acetoxybenzoic acid as much 40%, as shown by Run Nos. 4 and 14, wherein mole % yield increased from 57 mole % to 81 mole %, an increase of 23 mole %, and an increase of 40% over the 57 mole % of Run No. 4.

Comparison of Runs 12 and 196 illustrates the increase in yield obtained by using a decreased starting mole % of Ac₂O to pAAP in Run 12 and an increased amount of added Ac₂O in Run 12 during the reaction. Both Run Nos. 12 and 196 were at the same reaction temperature, 350° F. Runs 4 and 6 demonstrate the results of temperature effect, (Run 6 having a lower temperature and a yield of 81 mole % and Run 4 having a higher temperature and a yield of 57 mole %) all other process parameters being the same.

In the following Examples XI and XII, all reaction conditions except acetic anhydride addition were similar. In Example XI, a portion of the acetic anhydride was added at the beginning of the run and the remainder of acetic anhydride was added during the course of the run. In Example XII, all of the acetic anhydride was added at the beginning of the run. In each of these two examples, the reaction temperature was maintained at 300° F.

EXAMPLE XI

Fifteen (15) g (0.084 mole) of p-acetoxyacetophenone, 250 g (4.17 moles) of acetic acid, 90 g (0.88 mole) of acetic anhydride, 0.35 g (0.0014 mole) of Co-$(OAc)_2.4H_2O$, 0.35 g (0.0014 mole) of $Mn(OAc)_2.4H_2O$, and 0.47 g (0.0028 mole HBr) of 48% HBr were combined in a two-liter titanium-clad autoclave. The resulting mixture was heated to a temperature of 300° F. and the vessel was pressurized to 300 psi with nitrogen. Air was introduced at a rate of 0.45 scf/min and adjusted during the run to maintain a constant vent oxygen concentration (flow varied between 0.45 and 0.26 scf/min). During the run, over a period of 46 minutes, 133.9 g (0.75 mole) of p-acetoxyacetophenone, 160.8 g (1.58 moles) of acetic anhydride, and 39.8 g (0.66 mole) of acetic acid were added. The run was continued for an additional 17 minutes, until oxygen uptake ceased. The total run time was 63 minutes. Analyses of the reaction product and reactor wash provided the following yields: 83.4 mole % p-acetoxybenzoic acid, 0.46 mole % p-hydroxybenzoic acid, and 3.2 mole % unreacted p-acetoxyacetophenone.

EXAMPLE XII

Fifteen (15) g (0.084 mole) of p-acetoxyacetophenone, 90 g (1.50 moles) of acetic acid, 250 g (2.45 moles) of acetic anhydride, 0.35 g (0.0014 mole) of Co-$(OAc)_2.4H_2O$, 0.35 g (0.0014 mole) of $Mn(OAc)_2.4H_2O$, and 0.47 g (0.0028 mole HBr) of 48% HBr were introduced into a two-liter titanium-clad autoclave. The mixture was heated to a temperature of 300° F. and the reactor was pressurized to a pressure of 300 psi with nitrogen. Air was introduced at a rate of 0.39 scf/min and adjusted during the run to maintain a constant vent oxygen concentration (flow varied between 0.51 and 0.31 scf/min). During the run, over a period of 36 minutes, 133.9 g (0.75 mole) of p-acetoxyacetophenone and 200.9 g (3.35 moles) of acetic acid were added. The run was continued for an additional 16 minutes until oxygen uptake ceased. The total run time was 52 minutes. Analyses of the reaction product and the reactor wash provided the following yields: 72 mole % p-acetoxybenzoic acid, 0.34 mole % p-hydroxybenzoic acid, and 3.3 mole % unreacted p-acetoxyacetophenone.

A comparison of the yields obtained in runs conducted in Example XI and Example XII demonstrates that the semicontinuous addition of acetic anhydride during the length of the run provides higher yields of p-acetoxybenzoic acid. The test conducted in Example XI provides an embodiment of the process of the present invention and this embodiment produces a higher yield of the p-acetoxybenzoic acid than does the comparative run, the run exemplified in Example XII.

A second set of comparative runs was conducted at a temperature of 350° F. These runs are discussed hereinbelow in Examples XIII and XIV.

EXAMPLE XIII

Fifteen (15) g (0.084 mole) of p-acetoxyacetophenone, 90 g (1.50 moles) of acetic acid, 250 g (2.45 moles) of acetic anhydride, 0.35 g (0.0014 mole) of Co-$(OAc)_2.4H_2O$, 0.35 g (0.0014 mole) of $Mn(OAc)_2.4H_2O$, and 0.47 g (0.0028 mole HBr) of 48% HBr were introduced into a two-liter titanium-clad autoclave. The mixture was heated to a temperature of 350° F. and the reaction vessel was pressurized to a pressure of 350 psi with nitrogen. Air was introduced at a rate of 0.45 scf/min and adjusted during the run to maintain a constant vent oxygen concentration (the flow varied between 0.57 and 0.26 scf/min). During the run, over a period of 27 minutes, 133.9 g (0.75 mole) of p-acetoxyacetophenone and 200.9 g (3.35 moles) of acetic acid were added. The run was continued for an additional 18 minutes, until oxygen uptake ceased. Therefore, the total run time was 45 minutes. Analyses of the reaction product and reactor wash provided the following yields: 46.0 mole % p-acetoxybenzoic acid, 0.46 mole % p-hydroxybenzoic acid, 0.19 mole % p-hydroxyacetophenone, and 18.8 mole % unreacted p-acetoxyacetophenone.

EXAMPLE XIV

Fifteen (15) g (0.084 mole) of p-acetoxyacetophenone, 250 g (4.17 moles) of acetic acid, 15 g (0.15 mole) of acetic anhydride, 0.35 g (0.0014 mole) of Co-$(OAc)_2.4H_2O$, 0.35 g (0.0014 mole) of $Mn(OAc)_2.4H_2O$, and 0.47 g (0.0028 mole HBr) of 48% HBr were introduced into a two-liter titanium-clad autoclave. The resulting mixture was heated to a temperature of 350° F. and the reactor was pressurized to a pressure of 350 psi with nitrogen. Air was introduced into the reactor system at a rate of 0.45 scf/min to maintain a constant vent oxygen concentration. During the run, over a period of 30 minutes, 133.7 g (0.75 mole) of p-acetoxyacetophenone, 234.4 g (2.29 moles) of acetic anhydride, and 39.9 g (0.66 mole) of acetic acid were added. The run was continued for an additional 12 minutes, until oxygen uptake ceased. The total run time was, therefore, 42 minutes. Analyses of the reaction product and the reactor wash provided the following yields: 68.8 mole % p-acetoxybenzoic acid, 0.41 mole % p-hydroxybenzoic acid, and 4 mole % unreacted p-acetoxyacetophenone.

As was the case in the comparative tests of Examples XI and XII, the yield of p-acetoxybenzoic acid provided by the embodiment of the present invention, i.e., the run of Example XIV, produced a yield of p-acetoxybenzoic acid that was superior to that provided by the prior-art run of Example XIII.

The comparative tests presented in Examples XI through XIV demonstrate that embodiments of the process of the present invention, wherein a first portion of acetic anhydride is employed at the start of a run and a second portion of acetic anhydride is added during the run, provide an improvement over the prior-art process, wherein the acetic anhydride is put into the reactor solely at the beginning of the particular run. The increased yield of p-acetoxybenzoic acid resulting from the addition of acetic anhydride during the run, as well as the use of acetic anhydride at the start of the run, was unexpected. The process of the present invention is an improved process relative to the prior-art processes, since it provides improved yields of p-acetoxybenzoic acid.

What is claimed is:

1. A semicontinuous or continuous liquid-phase process for the production of p-acetoxybenzoic acid from p-acetoxyacetophenone in high yield, which process comprises: (a) oxidizing in a reaction zone said p-acetoxyacetophenone with a source of molecular oxygen in the presence of a catalyst comprising cobalt (II), manganese (II), and bromine, in a solvent comprising a lower aliphatic carboxylic acid and in the presence of a promoter consisting essentially of an acid anhydride of said lower aliphatic carboxylic acid, at a temperature within the range of from about 200° F. to about 400° F. and at a pressure of from 1 atmosphere to about 30 atmospheres, said promoter being present as an initial reactor charge in a mole ratio of promoter to said p-acetoxyacetophenone of from 1:1 to 2.4:1; (b) adding said promoter to said reaction zone during said oxidizing in an amount of from 0.25 to 1.5 moles of said promoter per mole of said p-acetoxyacetophenone, the total amount of promoter resulting from the initial charge and subsequent addition of said promoter providing a mole ratio of said promoter to said p-acetoxyacetophenone that is in the range of about 1.6:1 to 3:1 moles of said promoter per mole of said p-acetoxyacetophenone; (c) evaporating the reactor effluent to remove water and said lower aliphatic carboxylic acid therefrom; (d) recovering said lower aliphatic carboxylic acid that has been removed from said effluent; (e) recycling to a make-up vessel the lower aliphatic carboxylic acid that has been recovered from said effluent; (f) filtering the evaporator bottoms to recover reactor product from mother liquor; and (g) recycling said mother liquor to said reaction zone.

2. The process of claim 1, wherein said catalyst comprises a cobalt(II) compound, a manganese(II) compound, and a bromine compound.

3. The process of claim 1, wherein said catalyst comprises a cobalt(II) compound, a manganese(II) compound, a zirconium compound, and a bromine compound.

4. The process of claim 1, wherein the metal concentration of said catalyst is in the range of from about $1.0 \times 10^{-8}$ moles per mole of p-acetoxyacetophenone to about $4.0 \times 10^{-2}$ moles per mole of p-acetoxyacetophenone.

5. The process of claim 1, wherein said initial reactor charge of said promoter is in the range of from about 1:1 to 1.8:1 moles of said promoter per mole of p-acetoxyacetophenone.

6. The process of claim 1, wherein said lower aliphatic carboxylic acid is selected from the group consisting of acetic acid and propionic acid.

7. The process of claim 1, wherein said anhydride is selected from the group consisting of acetic anhydride and propionic anhydride.

8. The process of claim 1, wherein said lower aliphatic carboxylic acid is acetic acid and said anhydride is acetic anhydride.

9. The process of claim 1, wherein said source of molecular oxygen comprises air.

10. The process of claim 1, wherein said process is a semicontinuous process.

11. The process of claim 1, wherein said process is a continuous process.

12. The process of claim 1, wherein said process is a semicontinuous process, the temperature is in the range of from about 200° F. to about 350° F., and the pressure is in the range of from about 1 atmosphere to about 20 atmospheres.

13. The process of claim 1, wherein said process is a continuous process, the temperature is in the range of from about 200° F. to about 350° F., and the pressure is in the range of from about 1 atmosphere to about 20 atmospheres.

14. In an improved liquid-phase process for the production of p-acetoxybenzoic acid from p-acetoxyacetophenone in high yield, wherein said p-acetoxyacetophenone is oxidized with a source of molecular oxygen in a reaction zone in the presence of a catalyst comprising cobalt, manganese, and bromine, in a solvent comprising a lower aliphatic carboxylic acid and in the presence of a promoter consisting essentially of an acid anhydride of said lower aliphatic carboxylic acid, said process being a semicontinuous or continuous process, the improvement which comprises adding a first portion of said promoter as an initial reactor charge to said reaction zone and adding a second portion of said promoter to said reaction zone during the oxidation of said p-acetoxyacetophenone.

15. The improved process of claim 14, wherein said first portion of said promoter is added in an amount to provide a mole ratio of said promoter to said p-acetoxyacetophenone that is in the range of from about 1:1 to about 2.4:1.

16. The improved process of claim 14, wherein said second portion of said promoter is added to said reaction zone during the oxidation of said p-acetoxyacetophenone in an amount in the range of from about 0.25 to 1.5 moles of said promoter per mole of said p-acetoxyacetophenone, said amount of said second portion of said promoter being sufficient to provide an overall mole ratio of said promoter to said p-acetoxyacetophenone that is in the range of from about 1.6:1 to about 3:1 moles of said promoter per mole of said p-acetoxyacetophenone.

17. The improved process of claim 15, wherein said second portion of said promoter is added to said reaction zone during the oxidation of said p-acetoxyacetophenone in an amount in the range of from about 0.25 to 1.5 moles of said promoter per mole of said p-acetoxyacetophenone, said amount of said second portion of said promoter being sufficient to provide an overall mole ratio of said promoter to said p-acetoxyacetophenone that is in the range of from about 1.6:1 to about 3:1 moles of said promoter per mole of said p-acetoxyacetophenone.

* * * * *

UNITED STATES PATENT OFFICE
CERTIFICATE OF CORRECTION

Patent No. 4,873,361      Dated October 10, 1989

Inventor(s) Kristi A. Fjare

It is certified that error appears in the above-identified patent and that said Letters Patent is hereby corrected as shown below:

Abstract, Line 5    "carboxytlic" should be --carboxylic--

Col. 10, Line 26    "Reaction Temp., °F. 30" should be --Reaction Temp., °F 300--

Signed and Sealed this

Thirtieth Day of October, 1990

Attest:

HARRY F. MANBECK, JR.

Attesting Officer      Commissioner of Patents and Trademarks